United States Patent [19]

Tarnow et al.

[11] Patent Number: 4,840,969
[45] Date of Patent: Jun. 20, 1989

[54] N-SUBSTITUTED BENZAMIDES

[75] Inventors: Horst Tarnow, Langenfeld; Bernhard Homeyer, Leverkusen, both of Fed. Rep. of Germany

[73] Assignee: Bayer Aktiengesellschaft, Leverkusen, Fed. Rep. of Germany

[21] Appl. No.: 27,706

[22] Filed: Mar. 19, 1987

[30] Foreign Application Priority Data

Apr. 4, 1986 [DE] Fed. Rep. of Germany ....... 3611193

[51] Int. Cl.[4] .................... A01N 37/40; A01N 37/18; A01N 37/26
[52] U.S. Cl. .................... 514/617; 514/616; 514/618; 514/619; 514/622; 564/154; 564/156; 564/162; 564/166; 564/177; 564/183
[58] Field of Search ............... 564/156, 166, 183, 154, 564/162, 177; 514/616, 617, 619, 618, 622

[56] References Cited

U.S. PATENT DOCUMENTS

| | | | |
|---|---|---|---|
| 2,408,389 | 10/1946 | Gertler | 514/617 |
| 3,015,606 | 1/1962 | Walde | 514/619 |
| 3,161,564 | 12/1964 | Morehouse | 514/619 |
| 3,415,838 | 12/1968 | Crounse et al. | 564/166 X |
| 3,518,305 | 6/1970 | Welch et al. | 564/166 |
| 3,531,277 | 9/1970 | Lemin | 564/183 X |
| 3,655,752 | 4/1972 | Ackerman et al. | 564/156 |
| 3,709,938 | 1/1973 | Houlihan | 564/183 X |
| 3,823,134 | 7/1984 | Houlihan | 564/183 X |
| 3,825,594 | 7/1974 | Houlihan | 564/183 X |
| 3,835,189 | 9/1974 | Arsura et al. | 564/183 |
| 3,880,903 | 4/1975 | Rohr et al. | 564/183 X |
| 4,021,224 | 5/1977 | Pallos et al. | 564/156 X |
| 4,054,576 | 10/1977 | Baker et al. | 564/183 X |
| 4,119,789 | 10/1978 | Braus | 564/156 X |
| 4,505,859 | 3/1985 | Poindexter | 564/156 X |

FOREIGN PATENT DOCUMENTS

| | | | |
|---|---|---|---|
| 55399 | 9/1912 | Austria | 564/183 |
| 0039813 | 11/1981 | European Pat. Off. | |
| 0073974 | 3/1983 | European Pat. Off. | |
| 0122449 | 10/1984 | European Pat. Off. | |
| 2637947 | 3/1978 | Fed. Rep. of Germany | |
| 3018020 | 11/1981 | Fed. Rep. of Germany | |
| 3218966 | 3/1983 | Fed. Rep. of Germany | |
| 3217619 | 11/1983 | Fed. Rep. of Germany | |
| 3217620 | 11/1983 | Fed. Rep. of Germany | |
| 3307234 | 9/1984 | Fed. Rep. of Germany | |
| 57-93901 | 6/1982 | Japan | 424/324 |
| 268783 | 9/1950 | Switzerland | 564/183 |

OTHER PUBLICATIONS

Burger et al., CA 81:63427n (1974).
Bohme et al., Arch Pharm., vol. 294, No. 5, pp. 307–311 (1961).
Pesticidal Manual published by the British Corp. Protection Council, 5th edition (1977), p. 262.
J. Org. Chem., 24, 1256–1259 (1969).
J. Org. Chem., 27, 1406 (1962).
Isvest. Akad. Nauk. SSSR, Ser. Khim., 226–228 (1966).
Isvest. Akad. Nauk. SSSR, Ser. Khim., 1518–1523 (1966).
J. Med. Chem., 22, 1130–1133 (1979).
Ind. Eng. Chem., 48, 209–213 (1956).
J. Am. Chem. Soc., 102, 4958–4959 (1980).
Synthesis, 46 (1978).
Coll. Czech. Chem. Comm., 47, 2291–2305 (1982).

Primary Examiner—Charles F. Warren
Assistant Examiner—Carolyn S. Greason
Attorney, Agent, or Firm—Sprung Horn Kramer & Woods

[57] ABSTRACT

An N-substituted benzamide of the formula

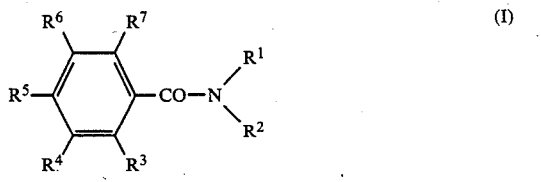

in which
 $R^1$ represents hydrogen or alkyl,
 $R^2$ represents halogenoalkyl with more than one carbon atom, or represents cycloalkyl which is substituted by halogen or halogenoalkyl and
 $R^3$, $R^4$, $R^5$, $R^6$ and $R^7$ are identical or different and represent hydrogen, halogen, nitro, alkyl, halogenoalkyl, halogenoalkoxy or halogenoalkylthio, or represent the radical—$CONR^1R^2$.

The N-substituted benzamides are active as insecticides and nematicides and can be prepared by reacting a benzoyl halide of the formula (II)

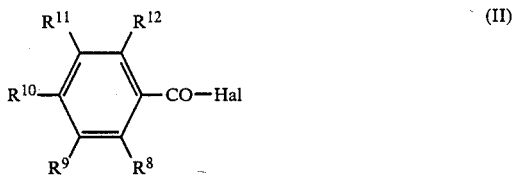

in which
 $R^8$, $R^9$, $R^{10}$, $R^{11}$ and $R^{12}$ are identical or different and represent hydrogen, halogen, nitro, alkyl, halogenoalkyl, halogenoalkoxy or halogenoalkylthio, or represent the radical —CO—Hal and Hal represents halogen,
with an amine of the formula (III)

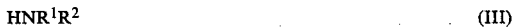

in which
 $R^1$ and $R^2$ have the abovementioned meanings, or with corresponding hydrohalides.

6 Claims, No Drawings

N-SUBSTITUTED BENZAMIDES

BACKGROUND OF THE INVENTION

1. Field of the Invention

The invention relates to new N-substituted benzamides, a process for their preparation and their use in agents for combating pests, in particular as insecticides and nematicides.

2. Background Information

It is known that certain phosphoric acid ester-amides, such as, for example, O-ethyl-O-(3-methyl-4-methylthio-phenyl)-N-isopropyl-phosphoric acid esteramide (common name: fenamiphos) have very good insecticidal and nematicidal properties (compare U.S. Pat. No. 2,978,479 and the *Pesticide Manual* published by the British Crop Protection Council, 5th edition (1977), page 262 with a description of the commercial product fenamiphos).

SUMMARY OF THE INVENTION

New N-substituted benzamides of the formula (I)

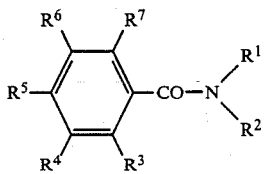

in which
R$^1$ represents hydrogen or alkyl,
R$^2$ represents halogenoalkyl with more than one carbon atom, or represents cycloalky which is substituted by halogen or halogenoalkyl and
R$^3$, R$^4$, R$^5$, R$^6$ and R$^7$ are identical or different and repesent hydrogen, halogen, nitro, alkyl, halogenoalkyl, halogenoalkoxy or halogenoalkylthio, or represent the radical —CONR$^1$R$^2$,
have now been found.

It has furthermore been found that the new N-substituted benzamides of the formula (I) are obtained by a process in which benzoyl halides of the formula (II)

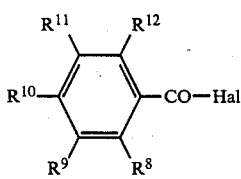

in which
R$^8$, R$^9$, R$^{10}$, R$^{11}$ and R$^{12}$ are identical or different and represent hydrogen, halogen, nitro, alkyl, halogenoalkyl, halogenoalkoxy or halogenoalkylthio, or represent the radical —CO—Hal and
Hal represents halogen,
are reacted with amines of the formula (III)

HNR$^1$R$^2$ (III)

in which
R$^1$ and R$^2$ have the abovementioned meanings, or the corresponding hydrohalides, if appropriate in the presence of acid acceptors and if appropriate in the presence of diluents.

The new N-substituted benzamides of the formula (I) are distinguished by a very good nematicidal and insecticidal action.

DETAILED DESCRIPTION OF THE INVENTION

The invention preferably relates to compounds of the formula (I) in which
R$^1$ represents hydrogen or alkyl with 1 to 6 carbon atoms,
R$^2$ represents halogenoalkyl with 2 to 8 carbon atoms and 1 to 12 halogen atoms, such as fluorine and/or chlorine, or represents cycloalkyl which has 3 to 8 carbon atoms and in substituted by halogen, such as fluorine and/or chlorine, or halogeno-C$_1$-C$_2$-alkyl and
R$^3$, R$^4$, R$^5$, R$^6$ and R$^7$ are identical or different and represent hydrogen, fluorine, chlorine, bromine, nitro, alkyl with 1 to 4 carbon atoms or halogenoalkyl, halogenoalkoxy or halogenoalylthio with in each case 1 to 4 carbon atoms in the alkyl part and 1 to 6 halogen atoms, such as fluorine and/or chlorine, or represent the radical —CONR$^1$R$^2$.

Particularly preferred new N-substituted benzamides of the formula (I) are those in which
R$^1$ represents hydrogen or alkyl with 1 to 4 carbon atoms,
R$^2$ represents halogenoalkyl with 2 to 6 carbon atoms and 1 to 8 fluorine or 1 to 8 fluorine and chlorine atoms, or represents cycloalkyl which has 3 to 6 carbon atoms and is substituted by fluorine, chlorine and/or trifluoromethyl and
R$^3$, R$^4$, R$^5$, R$^6$ and R$^7$ are identical or different and represent hydrogen, fluorine, chlorine, bromine, nitro, alkyl with 1 or 2 carbon atoms or halogenoalkyl, halogenoalkoxy or halogenoalkylthio with in each case 1 or 2 carbon atoms in the alkyl part and 1 to 4 fluorine and/or chlorine atoms, or represent the radical —CONR$^1$R$^2$. Especially preferred new compounds of the formula (I) are those in which
R$^1$ represents hydrogen, methyl, ethyl, n-propyl, i-propyl or n-butyl,
R$^2$ represents 2-fluoroethyl, 2,2-difluoroethyl, 2,2,2-trifluoroethyl, 3-fluoro-prop-1-yl, 3,3-difluoro-prop-1-yl, 3,3,3-trifluoro-prop-1-yl, 3-fluoro-prop-2-yl, 3,3-difluoro-prop-2-yl, 3,3,3-trifluoro-prop-2-yl, 2-fluoro-2-methyl-prop-2-yl, 2,2-difluoro-2-methyl-prop-2-yl, 2-methyl-2,2,2-trifluoro-prop-2-yl, 2-methyl-3,3,3-trifluoro-prop-1-yl, 2-methyl-3,3,3-chlorodifluoro-prop-1-yl, 2-methyl-3,3,3-dichlorofluoro-prop-1-yl, 1,3-difluoro-prop-2-yl, 1,1,1,3,3,3-hexafluoro-prop-2-yl, 3-fluoro-2-fluoromethyl-prop-2-yl, 1,3-difluoro-2-fluoromethyl-prop-2-yl, 1-trifluoromethylcycloprop-1-yl or 2,2-difluoro-cycloprop-1-yl and R$^3$, R$^4$, R$^5$, R$^6$ and R$^7$ are identical or different and represent hydrogen, fluorine, chlorine, bromine, nitro, methyl, trifluoromethyl, trifluoromethoxy or trifluoromethylthio, or represent the radical —CONR$^1$R$^2$.

If, for example, 2,6-difluorobenzoyl chloride and 2-amino-3,3,3-trifluoropropane are used as starting substances for the process according to the invention, the corresponding reaction can be outlined by the following equation:

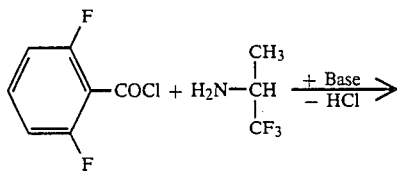

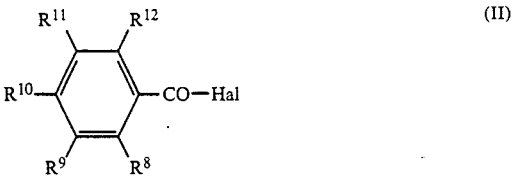

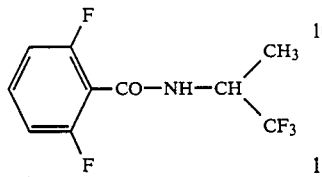

If, for example, o-phthalic acid dichloride and 1-amino-3,3,3-trifluoropropane are used as starting substances for the process according to the invention, the corresponding reaction can be outlined by the following equation:

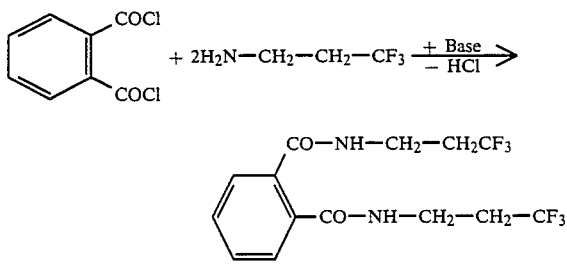

Formula (II) provides a general definition of the benzoyl halides to be used as starting substances in the process according to the invention. In this formula, $R^8$, $R^9$, $R^{10}$, $R^{11}$ and $R^{12}$ preferably represent hydrogen, fluorine, chlorine, bromine, nitro, $C_1$-$C_4$-alkyl, halogeno-$C_1$-$C_4$-alkyl, halogeno-$C_1$-$C_4$-alkoxy or halogeno-$C_1$-$C_4$-alkylthio. Hal represents halogen, such as, in particular, fluorine or chlorine.

The compounds of the formula (II) are known and/or can be prepared by known methods. In this context, see, for example, DE-AS (German Published Specification) No. 2,123,236, DE-OS (German Published Specification) No. 2,601,780, DE-OS (German Published Specification) No. 2,637,947, DE-OS (German Published Specification) No. 3,217,619, DE-OS (German Published Specification) No. 3,217,620 and EP-OS (European Published Specification) No. 122,449.

Examples which may be mentioned of the compounds of the formula (II) are:

TABLE 1

| $R^8$ | $R^9$ | $R^{10}$ | $R^{11}$ | $R^{12}$ |
|---|---|---|---|---|
| F | H | H | H | F |
| H | H | H | H | H |
| H | H | H | H | F |
| H | H | H | F | H |
| H | H | F | H | H |
| H | H | F | H | F |
| F | H | F | H | F |
| F | F | F | F | F |
| H | F | Cl | H | Cl |
| F | Cl | F | Cl | F |
| H | H | H | H | Cl |
| H | H | H | Cl | H |
| H | H | Cl | H | H |
| Cl | H | H | H | Cl |
| H | Cl | H | H | Cl |
| H | H | Cl | H | Cl |
| H | H | H | H | $CF_3$ |
| H | H | H | $CF_3$ | H |
| H | H | $CF_3$ | H | H |
| H | H | H | H | $CH_3$ |
| H | H | H | $CH_3$ | H |
| H | H | $CH_3$ | H | H |
| H | H | $NO_2$ | H | H |
| H | H | H | $NO_2$ | H |
| H | H | Cl | $NO_2$ | H |
| H | H | H | H | COCl |
| H | H | COCl | H | H |
| H | H | H | H | COF |
| H | H | COF | H | H |

Formula (III) provides a general definition of the amines also to be used as starting substances in the process according to the invention and the corresponding hydrohalides. In this formula (III), $R^1$ and $R^2$ preferably represent those radicals which have already been mentioned as preferred for these substituents in connection with the description of the substances of the formula (I) according to the invention. The hydrochlorides or the hydrobromides are preferably employed as the hydrohalides.

Examples which may be mentioned of the compounds of the formula (III) are:

$$HNR^1R^2 \qquad (III)$$

TABLE 2

| $R^1$ | $R^2$ | $R^1$ | $R^2$ |
|---|---|---|---|
| H | —$CH_2$—$CHF_2$ | H | —$CH_2$—$CF_3$ |
| H | —$CF_2$—$CF_3$ | H | —$CH_2$—$CF_2$—$CH_3$ |
| H | —$CH_2$—$CH_2$—$CHF_2$ | H | —$CH_2$—$CH_2$—$CHClF$ |
| H | —CH(CF$_3$)—$CH_2$—$CH_2$—$CH_3$ | H | —CH(CF$_3$)—$CH_2$—$CH_2$—$CF_3$ |
| H | —CH(CF$_3$)—CH(CH$_3$)$_2$ | H | —$CH_2$—$CH_2$—$CF_3$ |
| H | —$CH_2$—$CH_2$—$CClF_2$ | H | —$CH_2$—$CH_2$—$CCl_2F$ |
| H | —$CH_2$—$CHF$—$CF_3$ | H | —$CH_2$—$CF_2$—$CF_3$ |

TABLE 2-continued

| R¹ | R² | R¹ | R² |
|---|---|---|---|
| H | —CH₂—CH₂—CH₂—CF₃ | H | —CH(CH₃)(CF₃) |
| H | —C(CH₃)₂—CH₂F | H | —CH(CF₃)₂ |
| H | —C(CH₃)₂CF₃ | H | —CH₂—CH(CH₃)(CCl₂F) |
| H | —CH₂—CH(CH₃)(CClF₂) | H | —CH₂—CH(CH₃)(CF₃) |
| H | —CH(CF₃)—CH₂—CH₃ | H | —CH₂—CH₂F |
| H | —CH₂—CH₂—CH₂F | H | —CH(CH₃)—CH₂F |
| H | —CH(CH₃)—CHF₂ | H | —C(CH₃)₂—CHF₂ |
| H | —C(CH₃)(CH₂F)₂ | H | —C(CH₂F)₃ |
| H | —CH(CF₃)—(CH₂)₃—CH₃ | H | —CH(CF₃)—CH₂—CH(CH₃)₂ |
| H | —CH(CF₃)—(CH₂)₅—CH₃ | —CH₃ | —CH₂—CF₃ |
| —CH₃ | —CH₂—CH₂—CF₃ | —C₂H₅ | —CH₂—CF₃ |
| —C₃H₇—n | —CH₂—CF₃ | —C₄H₉—n | —CH₂—CF₃ |
| H | —CH(CH₂F)₂ | H | cyclopropyl-CF₃ (—C(CF₃)(CH₂—CH₂) ring) |
| H | cyclopropyl with two F (—CH—C(F)(F)—CH₂ ring) | | | and the corresponding hydrochlorides and -bromides of the abovementioned compounds of the formula (III).

The compounds of the formula (III) and the corresponding hydrohalides are known in some cases (compare, for example, *J. Org. Chem.*, 24, 1256–1259 (1969); *J. Org. Chem.*, 27, 1406–1409 (1962); *Isvest. Akad. Nauk. SSSR, Ser. Khim.* 1966, 226–228; *Isvest. Akad. Nauk. SSSR, Ser. Khim.*, 1966, 1518–1523; *J. Med. Chem.*, 22, 1130–1133 (1979); DE-OS (German Published Specification) No. 3,018,020; European Pat. No. A-39,813; DE-OS (German Published Specification) No. 3,218,966; European Pat. No. A-73,974; DE-OS (German Published Specification) No. 3,307,234; *Ind. Eng. Chem.*, 48, 209–213 (1956); *J. Am. Chem. Soc.*, 102, 4958–4959 (1980) and the preparation examples).

New amines which fall under the formula (III) are prepared, for example, as follows.

New amines of the formula $$X^3H_2C-\underset{\underset{CH_2X^2}{|}}{\overset{\overset{CH_2X^1}{|}}{C}}-NH_2 \qquad (IV)$$

in which the radicals $X^1$ to $X^3$ can be identical or different and represent hydrogen or fluorine, at least one of the radicals $X^1$ to $X^3$ representing fluorine, are obtained by a process in which, in preparation variant (A)

(a) the halogenated pivalic acid halides of the general formula (V)

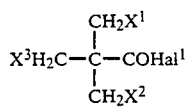

in which
$X^1$ to $X^3$ have the abovementioned meaning and
$Hal^1$ represents fluorine or chlorine, are converted, with a reagent which donates azide groups, into the fluorinated pivalic acid azides of the general formula (VI)

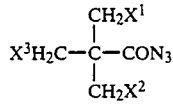

in which
$X^1$ to $X^3$ have the abovementioned meanings and (b) the compounds of the general formula (VI), which are isolated if appropriate, are decomposed under the influence of heat to give the fluorinated isocyanates of the general formula (VII)

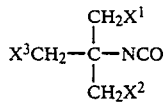

in which
$X^1$ to $X^3$ have the abovementioned meanings, and (c) the compounds of the general formula (VII), which are isolated if appropriate, are converted, for example by hydrochloric acid hydrolysis, into the fluorinated tertiary butylamine hydrochlorides of the general formula (VIII)

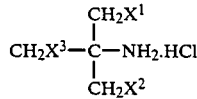

in which
$X^1$ to $X^3$ have the abovementioned meanings and (d) the compounds of the general formula (VIII), which are isolated if appropriate, are converted into the fluorinated tertiary butylamines of the general formula (IV) by treatment with a base, or are obtained by a process in which, in process variant (B), the isocyanates of the formula (VII)

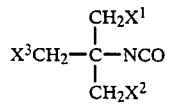

in which
$X^1$ to $X^3$ have the abovementioned meanings, are converted directly, by alkaline hydrolysis, into the fluorinated tertiary butylamines of the general formula (IV), or in that, in process variant (C), pivalic acid amides of the general formula (IX)

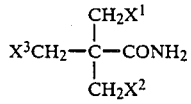

in which
$X^1$ to $X^3$ have the abovementioned meanings, are reacted with hypohalite.

New cyclopropylamines which fall under the formula (III), of the formula

are prepared, for example, by a process in which the known cyclopropylcarboxylic acid amines of the formula

are reacted with sulphur tetrafluoride in anhydrous hydrogen fluoride in an autoclave.

Cyclopropanecarboxylic acid amines of the formula (XI) are known (see, for example, *J. Chem. Soc.*, 1960, 2119–2132, ibid. 1962, 3977–3980; *Synthesis*, 1978, 46; and *Coll. Czech. Chem. Comm.*, 47, 2291–2305 (1982)).

The process according to the invention for the preparation of the new N-substituted benzamides of the formula (I) is preferably carried out using diluents. Possible diluents here are water and virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, amides, such as, for example, dimethylformamide, dimethylacetamide and N-methyl-pyrrolidone, and dimethylsulphoxide, tetramethylene sulphone and hexamethylphosphoric acid triamide.

Acid acceptors which can be employed in process according to the invention are all the acid-binding agents which can usually be employed for such reactions. Preferred possible acid-binding agents are alkali metal hydroxides, such as, for example, sodium and potassium hydroxide, alkaline earth metal hydroxides, such as, for example, calcium hydroxide, alkali metal carbonates and alcoholates, such as sodium and potassium carbonate and sodium and potassium methylate and ethylate, and furthermore aliphatic, aromatic or heterocyclic amines, for example triethylamine, trimethylamine, dimethylaniline, dimethylbenzylamine, pyridine, quinoline, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO). It is also possible for the amines of the formula (III) to be employed in excess and for the excess amine to act as the acid-binding agent.

The reaction temperatures can be varied within a substantial range in the process according to the invention. The reaction is in general carried out at temperatures between 0° C. and 100° C., preferably at temperatures between 20° C. and 80° C. In the case of reactive amines, it is usually scarcely necessary to warm the mixture, because the reaction already proceeds of its own accord. If amines which are slow to react are used in the reaction according to the invention, heating for several hours may be necessary.

The reactions are in general carried out under normal pressure. In the case of volatile amines which are slow to react, however, it may be advantageous to carry out the reaction in closed vessels under increased pressure.

In carrying out the process according to the invention, 1.00 to 1.6 mol, preferably 1.05 to 1.3 mol, of amine of the formula (III) and 1 to 3 mol, preferably 1 to 2 mol of acid acceptor or a further mol of the amine of the formula (III) are preferably employed per radical of —CO—Hal in the benzoyl halide of the formula (II). The reaction mixture is worked up by customary methods. The compounds of the formula (I) are usually obtained in the solid form or can be precipitated by addition of water—if appropriate after concentration of the reaction solutions.

The active compounds are suitable for combating animal pests, in particular insects and nematodes, encountered in agriculture, in forestry, in the protection of stored products and of materials, and in the hygiene field, and have good plant tolerance and favorable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and *Scutigera* spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria.* From the order of the Dermaptera, for example, *Forficula auricularia.* From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicornye brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiuella, Homona magnanima* and *Tortrix viridana.* From the order of the Coleoptera, for example, *Anobium punctatum, Rhizopertha dominica, Acanthoscelides obtectus, Hylotrupes bajulus, Agelastica alni, Leptinotarsa decem-lineata, Phaedon cochleariae,* Diabrotica spp., *Psylliodes chrysocephala, Epilachna varivestis,* Atomaria spp., *Oryzae-philus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solsti-tialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.* From the order of the Siphonaptera, for example, *Xenopsylla cheopis* and Ceratophyllus spp. From the order of the Arachnida, for example, *Scorpio maurus* and *Latrodectus mactans.*

The phytoparasitic nematodes include Pratylenchus spp, *Radopholus similis, Ditylenchus dipsaci, Tylenchulus semipenetrans,* Heterodera spp., Meloidogyne spp., Aphelenchoides spp., Longidorus spp., Xiphinema spp. and Trichodorus spp..

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by, mixing the active compounds with extenders, that is, liquid solvents, liquefied gases under pressure, and/or solid carriers, optionally with the use of surface-active agents, that is emulsifying agents and-/or dispersing agents, and/or foam-forming agents. In the case of the use of water as an extender, organic solvents can, fo example, also be used as auxiliary solvents. As liquid solvents, there are suitable in the main:

aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example, mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example, alkylaryl polyglycol ethers, alkyl sulphonates, alkyl sulphates, aryl sulphonates as well as albumin hydrolyzation products; as dispersing agents there are suitable: for example, lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example, iron oxide, titanium oxide and Prussian blue, and organic dyestuffs, such as alizarin dyestuffs,azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

As already stated above, as compared with corresponding known compounds the new compounds of the formula (I) according to the invention surprisingly exhibit a particularly favorable toxicity the warm-blooded animals and at the same time a very good activity against animal pests. These properties can in many cases considerably facilitate the use of the active compounds, especially in cases where no sufficiently experienced personnel are available during application and observance of the customary safety measures and caution necessary in combating pests cannot be completely guaranteed.

PREPARATION EXAMPLES

Example 1

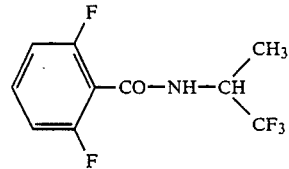

17.65 g (0.1 mol) of 2,6-difluorobenzoyl chloride, dissolved in 50 ml of toluene, are added dropwise to a solution of 11.30 g (0.1 mol) of 2-amino-1,1,1-trifluoropropane and 13.5 g (0.1 mol) of N,N-dimethylbenzylamine in 200 ml of toluene at 20° C.–30° C. and the mixture is stirred at 50° C.–60° C., N,N-dimethylbenzylamine hydrochloride precipitating. The mixture is then cooled to 20° C. and extracted with water and the organic phase is concentrated in vacuo. The colorless residue is recrystallized from wash benzine and/or toluene.

21.6 g (85.4% of theory) of 2,6-difluorobenzoic acid N-(1,1,1-trifluoro-prop-2-yl)-amide of melting point 167° C.–168° C. are obtained.

EXAMPLE 2

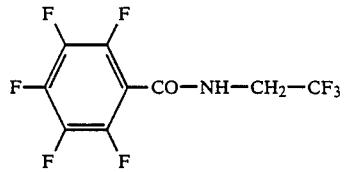

21.4 g (0.1 mol) of 2,3,4,5,6-pentafluorobenzoyl fluoride, dissolved in 50 ml of toluene, are added dropwise to a solution of 9.9 g (0.1 mol) of 2,2,2-trifluoro-1-amino-ethane and 13.5 g (0.1 mol) of N,N-dimethylbenzylamine in 250 ml of toluene at 20° C.–30° C. The mixture is then stirred at 50° C.–60° C. and cooled to 20° C., water is added and the solid reaction product is filtered off with suction. The residue is washed with water and dried.

25.2 g (86% of theory) of 2,3,4,5,6-pentafluorobenzoic acid N-(2,2,2-trifluoroethyl)-amide are obtained.

EXAMPLE 3

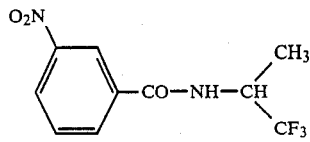

18.55 g (0.01 mol) of 3-nitrobenzoyl chloride in 50 ml of toluene are added dropwise to a mixture of 14.95 g (0.1 mol) of 2-amino-1,1,1-trifluoropropane hydrochloride and 27 g (0.2 mol) of N,N-dimethylbenzylamine in 250 ml of toluene at 20° C.-30° C. The mixture is then stirred at 50° C.-60° C. After cooling to 20° C., water is added and the solid reaction product is filtered off with suction. The residue is washed with water and dried.

19.8 g (75.6% of theory) of 3-nitro-benzoic acid N-(1,1,1-trifluoro-prop-2-yl)-amide of melting point 130° C.-131° C. are obtained.

EXAMPLE 4

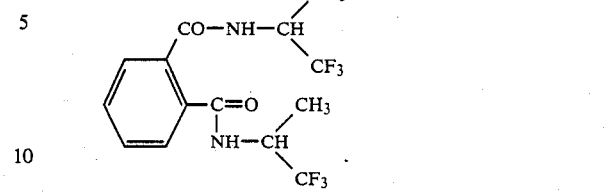

20.3 g (0.1 mol) of o-phthalyl chloride, dissolved in 100 ml of toluene, are added dropwise to a solution of 22.6 g (0.2 mol) of 2-amino-1,1,1-trifluoropropane and 27.0 g (0.2 mol) of N,N-dimethylbenzylamine in 300 ml of toluene at 20° C.-30° C. The mixture is then stirred at 50° C.-60° C. After cooling to 20° C., water is added and the solid reaction product is filtered off with suction. The residue is washed with water and dried.

29.2 g (82% of theory) of o-phthalic acid bis-[N-(1,1,1-trifluoro-prop-2-yl)-amide of melting point 230° C.-231° C. are obtained.

The following compounds of the formula (I) can be prepared analogously to Example 1 to 4:

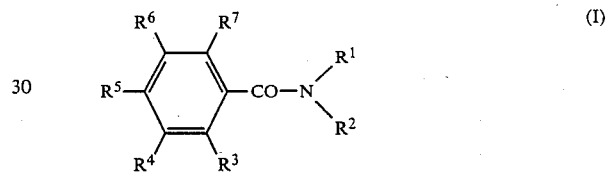

TABLE 3

| Example No. | $R^1$ | $R^2$ | $R^3$ | $R^4$ | $R^5$ | $R^6$ | $R^7$ | Melting point [°C.] |
|---|---|---|---|---|---|---|---|---|
| 5 | H | —CH$_2$CF$_3$ | F | H | H | H | F | 107–109 |
| 6 | CH$_3$ | —CH$_2$CF$_3$ | F | H | H | H | F | 79–81 |
| 7 | H | —CH$_2$—CH(CH$_3$)(CClF$_2$) | F | H | H | H | F | 98–100 |
| 8 | H | —CH$_2$—CH(CH$_3$)(CCl$_2$F) | F | H | H | H | F | 73–75 |
| 9 | H | —CH$_2$CH$_2$CF$_3$ | F | H | H | H | F | 74–76 |
| 10 | H | —C(CH$_3$)$_2$CH$_2$F | F | H | H | H | F | 128–130 |
| 11 | H | —C(CH$_3$)$_2$CF$_3$ | F | H | H | H | F | 105–107 |
| 12 | H | —CH$_2$CH$_2$CF$_3$ | H | H | Cl | H | H | 114–116 |
| 13 | H | —CH$_2$CH$_2$CF$_3$ | H | F | Cl | H | Cl | 88–89 |
| 14 | H | —CH$_2$CH$_2$CF$_3$ | F | F | F | F | F | 75–76 |
| 15 | H | —CH$_2$CH$_2$CF$_3$ | H | H | H | CH$_3$ | H | 58–60 |
| 16 | H | —C(CH$_3$)$_2$CF$_3$ | H | H | H | H | Cl | 82–83 |
| 17 | H | —CH$_2$CH$_2$CF$_3$ | H | H | H | CF$_3$ | H | $n_D^{20}$: 1.4465 |
| 18 | H | —CH(CH$_3$)(CF$_3$) | F | F | F | F | F | 150–151 |
| 19 | H | —CH$_2$CF$_3$ | F | Cl | F | Cl | F | 131–132 |
| 20 | H | —CH$_2$CH$_2$CF$_3$ | F | Cl | F | Cl | F | 118–120 |

TABLE 3-continued

| Example No. | R¹ | R² | R³ | R⁴ | R⁵ | R⁶ | R⁷ | Melting point [°C.] |
|---|---|---|---|---|---|---|---|---|
| 21 | H | —CH(CH₃)(CF₃) | F | Cl | F | Cl | F | 175–177 |
| 22 | H | —CH₂CF₃ | H | F | Cl | H | Cl | 126–128 |
| 23 | H | —CH(CH₃)(CF₃) | H | F | Cl | H | Cl | 137–139 |
| 24 | H | —CH₂CF₃ | H | H | H | H | CF₃ | 125–127 |
| 25 | H | —CH(CH₃)(CF₃) | H | H | H | H | CF₃ | 118–120 |
| 26 | H | —CH(CH₃)(CF₃) | H | H | H | H | H | 102–103 |
| 27 | H | —CH(CH₃)(CF₃) | H | H | Cl | H | H | 130–131 |
| 28 | H | —CH(CH₃)(CF₃) | H | H | NO₂ | H | H | 110–112 |
| 29 | H | —CH(CH₃)(CF₃) | H | H | H | H | Cl | 128–129 |
| 30 | H | —CH₂CH₂CF₃ | H | H | CH₃ | H | H | 118–120 |
| 31 | H | —CH₂CF₃ | H | H | —CONH—CH₂CF₃ | H | H | >250 |
| 32 | H | —CH₂CH₂CF₃ | H | H | —CONH—CH₂CH₂CF₃ | H | H | 211–212 |
| 33 | H | —C(CF₃)(CH₂CH₂) (cyclopropyl) | F | H | H | H | F | 174–175 |
| 34 | H | —CH(CH₂F)₂ | F | H | H | H | F | 122–124 |
| 35 | H | —CH(CH₃)(CF₃) | H | H | H | CF₃ | H | 77–78 |
| 36 | H | —CH(CH₃)(CF₃) | H | H | H | Cl | H | 94–95 |
| 37 | H | —C(CH₂F)₂CH₃ | F | H | H | H | F | 119–120 |
| 38 | H | —C(CH₃)₂CH₂F | H | F | Cl | H | Cl | 80–81 |

TABLE 3-continued

| Example No. | R$^1$ | R$^2$ | R$^3$ | R$^4$ | R$^5$ | R$^6$ | R$^7$ | Melting point [°C.] |
|---|---|---|---|---|---|---|---|---|
| 39 | H | —CH$_2$—CH(CH$_3$)(CCl$_2$F) | H | F | Cl | H | Cl | 76–78 |
| 40 | H | —CH$_2$—CH(CH$_3$)(CClF$_2$) | H | H | H | H | Cl | 98–99 |
| 41 | H | —CH(CH$_3$)(CF$_3$) | F | H | H | H | F | 177–178 |
| 42 | H | —CH(CH$_3$)(CF$_3$) | H | H | H | H | F | 82 |
| 43 | H | —C(CH$_3$)$_2$CF$_3$ | H | H | H | H | F | n$_D^{20}$: 1,4674 |
| 44 | H | —CH$_2$CH$_2$CF$_3$ | H | H | H | H | F | 67 |
| 45 | H | —CH$_2$CF$_3$ | H | H | H | H | F | 88 |
| 46 | CH$_3$ | —CH$_2$CF$_3$ | H | H | H | H | F | n$_D^{20}$: 1,4655 |
| 47 | CH$_3$ | —CH$_2$CF$_3$ | H | H | CF$_3$ | H | H | n$_D^{20}$: 1,4438 |
| 48 | H | —CH$_2$CF$_3$ | H | H | CF$_3$ | H | H | 116 |
| 49 | H | —CH$_2$CH$_2$CF$_3$ | H | H | CF$_3$ | H | H | 108 |
| 50 | H | —CH(CH$_3$)(CF$_3$) | H | H | CF$_3$ | H | H | 131 |
| 51 | CH$_3$ | —CH$_2$CF$_3$ | F | F | CF$_3$ | F | F | n$_D^{20}$: 1,4199 |
| 52 | H | —CH$_2$CF$_3$ | F | F | CF$_3$ | F | F | 118 |
| 53 | H | —CH$_2$CH$_2$CF$_3$ | F | F | CF$_3$ | F | F | 118 |
| 54 | H | —CH(CH$_3$)(CF$_3$) | F | F | CF$_3$ | F | F | 124 |

Starting compounds of the formula (III) and (IIIa)

EXAMPLE (III-1)

H$_2$N—CH(CH$_2$F)$_2$ 45 g (0.2 mol) of N-(1,3-difluoro-2-propyl)-phthalimide are suspended in 100 ml of water and, after addition of 200 ml of concentrated hydrochloric acid, the mixture is heated at the reflux temperature for 5 hours. The solid (phthalic acid) which has precipitated after cooling is filtered off, the filtrate is extracted with 20% strength aqueous sodium hydroxide solution and the extracts are dried over magnesium sulphate. After the solvent has been distilled off under normal pressure, the residue is fractionated under a waterpump vacuum.

13.5 g (71% of theory) of 2-(1,3-difluoro)-propylamine of boiling point 30°–34° C./50 mbar and refractive index n$_D^{20}$=1.3802 are obtained.

EXAMPLE (IIIA-1)

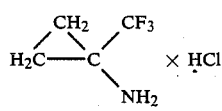

40 g (0.4 mol) of 1-amino-cyclopropanecarboxylic acid are reacted with 100 g of SF$_4$ and 50 ml of HF in a V$_4$A stirred autoclave at 120° C. under the autogenous pressure (25–30 bar) for 8 hours. After the volatile constituents have been distilled off, the mixture is rendered alkaline with 45% strength sodium hydroxide solution and the product is then separated off by steam distillation. The steam distillate is acidified with concentrated hydrochloric acid.

After concentration and drying, 40 g (62% of theory) of 1-trifluoromethyl-cyclopropylamine hydrochloride of melting point >260° C. are obtained.

EXAMPLE (IIIA-2)

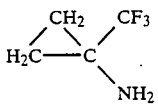

44 g (0.22 mol) of 20% strength aqueous sodium hydroxide solution are added dropwise to 32.4 g (0.2 mol) of 1-trifluoromethylcyclopropylamine hydrochloride from Example (IIIa-1) at an oil bath temperature of 80° C.–90° C. in the course of about 15 minutes. The amine liberated is distilled off at the same time. After drying over magnesium sulphate, the product is redistilled.

22 g (89% of theory) of 1-trifluoromethylcyclopropylamine of refractive index $n_D^{20}=1.3483$ are obtained.

The flavorable toxicity of the new compounds of the formula (I) to warm-blooded animals can be demonstrated by the following comparison values:

EXAMPLE A

LD$_{50}$ values on rats (oral)

| Active compound | LD$_{50}$ (mg of active compound/kg of body weight) |
|---|---|
| fenamiphos (common name) prior art (A) | 10–20 |
| (1) | >1000 |

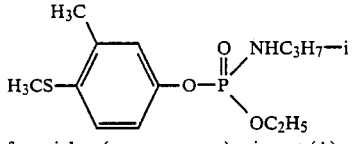
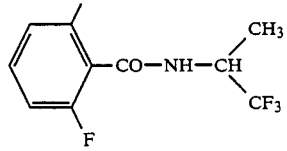

The values were determined in the customary manner. The active compounds were dissolved in polyethylene glycol "Lutrol" (trademark of BASF AG, Ludwigshafen, German Federal Republic) and the solution was administered to the rats with a stomach tube.

EXAMPLE B

Critical concentration test
Test nematode: Globodera rostochiensis
Solvent: 3 parts by weight of acetone
Emulsifier: 1 part by weight of alkylaryl polyglycol ether To produce a suitable preparation of active compound, 1 part by weight of active compound is mixed with the stated amunt of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance here, only the amount of active compound per unit volume of soil, which is given in ppm, being decisive. The treated soil is filled into pots, potatoes are planted and the pots are kept at a greenhouse temperature of 18° C.

After six weeks, the potato roots are examined for cysts and the degree of effectiveness of the active compound is determined in %. The degree of effectiveness is 100% if infestation is completely avoided and is 0% if the infestation is just as high as in the case of the control plants in untreated soil which has been infested in the same manner.

In this test, for example, the compounds according to the invention of preparation examples (1), (5), (29) and (33) and the known compound (A) exhibit a degree of effectiveness of 95% of active compound concentrations of 2.5, 5 and 10 ppm.

EXAMPLE C

Critical concentration test/nematodes
Test nematode: Meloidogyne incognita
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is of practically no importance here, only the amount of active compound per unit volume of soil, which is give in ppm, being decisive. The treated soil is filled into pots, lettuce is sown and the pots are kept at a greenhouse temperature of 27° C.

After four weeks, the lettuce roots are examined for infestation with nematodes (root galls), and the degree of effectiveness of the active compound is determined in %. The degree of effectiveness is 100% if infestation is completely avoided and is 0% if the infestation is just as high as in the case of the control plants in untreated soil which has been infested in the same manner.

In this test, compounds (1), (6), (29) and (33) according to the invention and the known compound (A) show a degree of effectiveness of 95% at an active compound concentration of 1.25 ppm–10 ppm.

It will be appreciated that the instant specification and claims are set forth by way of illustration and not limitation, and that various modifications and changes may be made without departing from the spirit and scope of the present invention.

We claim:

1. A method of combating insects and nematodes comprising applying to said insects or nematodes or to a habitat thereof, an insecticidal or nematicidal effective amount of an N-substituted benzamide of the formula (I)

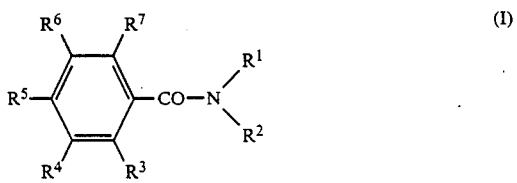

in which
R$^1$ represents hydrogen or alkyl,

R² represents halogenoalkyl with more than one carbon atoms, or represents cycloalkyl which is substituted by halogen or halogenoalkyl and R³, R⁴, R⁵, R⁶ and R⁷ are identical or different and represent hydrogen, halogen, nitro, alkyl, halogenalkyl, halogenoalkoxy or halogenoalkylthio, or represent the radical —CONR¹R².

2. A method of combating insects and nematodes according to claim 1, wherein in formula (I), R¹ represents hydrogen or alkyl with 1 to 6 carbon atoms, R² represents halogenoalkyl with 2 to 8 carbon atoms and 1 to 12 halogen atoms, or represents cycloalkyl which has 3 to 8 carbon atoms and is substituted by halogen, or halogeno-$C_1$-$C_2$-alkyl and R³, R⁴, R⁵, R⁶ and R⁷ are identical or different and represent hydrogen, fluorine, chlorine, bromine, nitro, alkyl with 1 to 4 carbon atoms or halogenoalkyl, halogenoalkoxy or halogenoalkylthio with in each case 1 to 4 carbon atoms in the alkyl part and 1 to 6 halogen atoms, or represent the radical —CONR¹R².

3. A method of combating insects and nematodes according to claim 2, wherein for R² said halogen is selected from the group consisting of fluorine and chlorine.

4. A method of combating insects and nematodes according to claim 1 wherein the formula (I), R¹ represent hydrogen or alkyl with 1 to 4 carbon atoms, R² represents halogenoalkyl with 2 to 6 carbon atoms and 1 to 8 halogen atoms, wherein said halogen atoms are selected from the group consisting of (a) fluorine atoms and (b) fluorine and chlorine atoms, or represents cycloalkyl which has 3 to 6 carbon atoms and is substituted by fluorine, chlorine and/or trifluoromethyl and R³, R⁴, R⁵, R⁶ and R⁷ are identical or different and represent hydrogen, fluorine, chlorine, bromine, nitro, alkyl with 1 or 2 carbon atoms or halogenalkyl, halogenoalkoxy or halogenoalkylthio with in each case 1 or 2 carbon atoms in the alkyl part and 1 to 4 halogen atoms, wherein said halogen atoms are selected from the group consisting of (a) fluorine atoms, (b) chlorine atoms and (c) fluorine and chlorine atoms, or represent the radical —CONR¹R².

5. A method of combating insects and nematodes according to claim 1 wherein in the formula (I), R¹ represents hydrogen, methyl, ethyl, n-propyl, i-propyl or n-butyl, R² represents 2-fluoroethyl, 2,2-difluoroethyl, 2,2,2-trifluoroethyl, 3-fluoro-prop-1-yl, 3,3-difluoro-prop-1-yl, 3,3,3-trifluoro-prop-1-yl, 3-fluoro-prop-2-yl, 3,3-difluoro-prop-2-yl, 3,3,3-trifluoro-prop-2-yl, 2-fluoro-2-methyl-prop-2-yl, 2,2-difluoro-2-methyl-prop-2-yl, 2-methyl-2,2,2-trifluoro-prop-2-yl, 2-methyl-3,3,3-trifluoro-prop-1-yl, 2-methyl-3,3,3-chlorodifluoro-prop-1-yl, 2-methyl-3,3,3-dichlorofluoro-prop-1-yl, 1,3-difluoro-prop-2-yl, 1,1,1,3,3,3-hexafluoro-prop-2-yl, 3-fluoro-2-fluoromethyl-prop-2-yl, 1,3-difluoro-2-fluoromethyl-prop-2-yl, 1-trifluoromethylcycloprop-1-yl or 2,2-difluoro-cycloprop-1-yl and R³, R⁴, R⁵, R⁶ and R⁷ are identical or different and represent hydrogen, fluorine, chlorine, bromine, nitro, methyl, trifluoromethyl, trifluoromethoxy or trifluoromethylthio, or represent the radical —CONR¹R².

6. A method of combating insects and nematodes according to claim 1, wherein the N-substituted benzamide is selected from the group consisting of 2,6-difluorobenzoic acid N-(1,1,1-trifluoro-prop-2-yl)-amide,

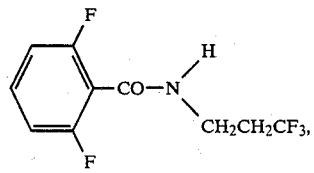

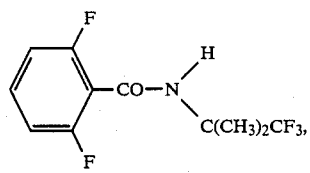

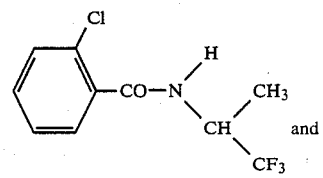

and

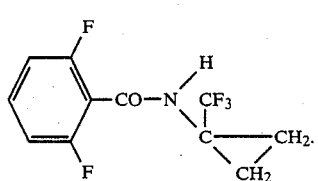

* * * * *

UNITED STATES PATENT AND TRADEMARK OFFICE
CERTIFICATE OF CORRECTION

PATENT NO. : 4,840,969

DATED : June 20, 1989

INVENTOR(S) : Tarnow et al

It is certified that error appears in the above-identified patent and that said Letters Patent is hereby corrected as shown below:

On title page item [56], U.S. PATENT DOCUMENTS: After "3,823,134" delete 7/1984 " and substitute — 7/1974. Add — 3,324,178, 6/1967, Newallis — After " 4,119,789, 10/1978, Braus " add — et al. — FOREIGN PATENT DOCUMENTS: Add — 0226837, 7/1987, Europe . —

Col. 2, line 23   Delete " halogenoalylthio " and substitute — halogenoalkylthio —

Col. 4, line 9    Before " TABLE 1 " add — Hal=chlorine or fluorine —

Col. 9, line 65   Delete " Brevicornye " and substitute — Brevicoryne —

Col. 10, line 17  Delete " ambivella " and substitute — ambiguella —

Col. 19, line 60  Delete " amunt " and substitute — amount —

Signed and Sealed this

Nineteenth Day of January, 1993

*Attest:*

DOUGLAS B. COMER

*Attesting Officer*      *Acting Commissioner of Patents and Trademarks*